United States Patent [19]
Breuer et al.

[11] 3,969,365
[45] July 13, 1976

[54] 4-(1,2,4-OXADIAZOLYLFORMAMIDOALKYL)-PHENYLSULFONYL UREAS

[75] Inventors: Hermann Breuer, Burgweinting; Ivo Polacek, Regensburg, both of Germany

[73] Assignee: E. R. Squibb & Sons, Inc., Princeton, N.J.

[22] Filed: Feb. 17, 1972

[21] Appl. No.: 227,276

[52] U.S. Cl. ................. 260/307 G; 260/329 R; 260/346.1 R; 260/453 A; 424/272
[51] Int. Cl.² ........................................ C07D 271/06
[58] Field of Search ........................... 260/307 G

[56] References Cited
UNITED STATES PATENTS
2,367,056  1/1945  Roblin et al. ............... 260/239.6

*Primary Examiner*—Nicholas S. Rizzo
*Assistant Examiner*—Diana G. Rivers
*Attorney, Agent, or Firm*—Lawrence S. Levinson; Merle J. Smith

[57] ABSTRACT

4-(1,2,4-Oxadiazolylformamidoalkyl)phenylsulfonyl ureas e.g. 1-cyclohexyl-3-[p-β-(5-methyl-1,2,4-oxadiazole-3-carbonylaminoethyl)phenylsulfonyl-]urea, are useful as anti-inflammatory and hypoglycemic agents.

11 Claims, No Drawings

4-(1,2,4-OXADIAZOLYLFORMAMIDOALKYL)-PHENYLSULFONYL UREAS

OBJECTS OF THE INVENTION

It is an object of the present invention to prepare new compounds which are effective anti-inflammatory and hypoglycemic agents. A further object is to provide a method for the preparation of these compounds. These and other objects of the present invention will be apparent from the following description.

SUMMARY OF THE INVENTION

The compounds of the invention have the formula:

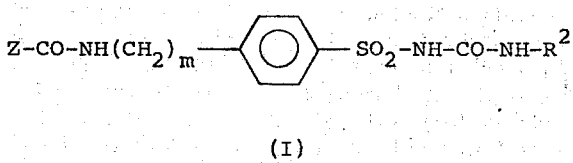

(I)

wherein:
Z may be an oxadiazole radical of the formula

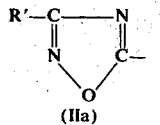 or 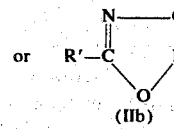

(IIa)　(IIb)

wherein R' may be hydrogen, a straight or branched chain alkyl or alkenyl radical of from 1 to 6 carbon atoms, a cycloalkyl radical of from 3 to 6 carbon atoms, cycloalkyl-alkyl wherein the cycloalkyl moiety may have from 3 to 6 carbon atoms and the alkyl moiety may have from 1 to 4 carbon atoms, $(R^3)_n$-phenyl, $(R^3)_n$-phenylalkyl wherein the alkyl moiety may have from 1 to 4 carbon atoms, $R^3$ may be hydrogen, an alkyl or alkoxy radical of from 1 to 4 carbon atoms, F, Cl or Br, and $n$ may be 0, 1, 2 or 3; $m$ may be 1, 2 or 3; and $R^2$ may be:

1. hydrogen, a straight or branched chain alkyl or alkenyl radical of from 1 to 6 carbon atoms, mercaptoalkyl of from 2 to 8 carbon atoms, or phenyl;
2. a radical of the formula $-(CH_2)_p-E-(CH_2)_q CH_3$ wherein E may be oxygen, sulfur or sulfonyl; $p$ may be from 2 to 7; and $q$ may be 0 to 5; the sum of $p + q$ being from 3 to 7;
3. phenylalkyl wherein the alkyl radical may have from 1 to 3 carbon atoms or phenylcycloalky wherein the cycloalkyl radical has from 3 to 8 carbon atoms;
4. cycoalkyl or cycloalkenyl of from 3 to 8 carbon atoms or alkyl-substituted cycloalkyl or cycloalkenyl wherein the alkyl radical may have from 1 to 3 carbon atoms;
5. endoalkylene cycloalkyl, endoalkylene cycloalkenyl, bisendoalkylene cycloalkyl or bisendoalkylene cycloalkenyl wherein the endoalkylene part may have from 1 to 4 carbon atoms and the cycloalkyl or cycloalkenyl part may have from 5 to 8 carbon atoms;
6. a saturated, mono- or di-unsaturated heterocyclic ring containing from 4 to 6 carbon atoms and an oxygen atom or a sulfur atom or a nitrogen atom;
7. a saturated, mono- or di-unsaturated heterocyclic ring linked to the nitrogen atom by means of a methylene group and containing from 4 to 5 carbon atoms and either an oxygen or a sulfur atom.

Preferred compounds are those wherein R' is a straight or branched chain alkyl radical of from 1 to 6 carbon atoms, or phenyl, and $R^2$ is cyclohexyl.

DETAILED DESCRIPTION

The compounds of the present invention may be prepared by the following series of reactions:

A 1,2,4-oxadiazole carboxylic acid ester of the formula $$ZCO_2R^4 \quad (III)$$

wherein Z is as previously defined and $R^4$ is a straight or branched chain aliphatic radical of up to 20 carbon atoms which may be mono- or diunsaturated is reacted with p-aminoalkyl)-benzenesufonamide of the formula

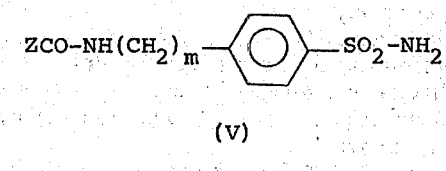

(IV)

to yield a compound of the formula

(V)

Alternatively, a compound of formula V may be prepared by reacting a 1,2,4-oxadiazole acyl halide of the formula $$ZCOX \quad (VI)$$

wherein X is chlorine or bromine, with a compound of formula IV in the presence of an acid binding agent.

The compounds of formula I may then be prepared by reacting a compound of formula V, or an alkali metal or alkaline earth metal salt thereof, with an $R^2$-substituted isocyanate. It will be obvious to those skilled in the art that the isocyanate group of the $R^2$-substituted isocyanate may be replaced by an isothiocyanate, a carbamic acid ester, a thiocarbamic acid ester, a carbamic acid halide or a urea. If an isothiocyanate is used, the resulting thiourea is subsequently hydrolyzed to the urea.

The 1,2,4-oxadiazole carboxylic acid esters of formula III and the corresponding acyl halides of formula VI are known compounds which are prepared according to known methods, e.g., Fortschritte der Chemischen Forschung, Volume 4, Part 4, pages 845–846 (1965).

The p-(aminoalkyl)phenylsulfonamides of formula IV are known compounds which may be readily prepared, for example, by reacting an N-protected acylated phenylalkylamine with $HOSO_2Cl$ to form the p-(N-acylated aminoalkyl)phenylsulfonyl chloride, reacting the latter with ammonia to form the corresponding sulfonamide, and removing the protecting acyl group according to known techniques.

The $R^2$-substituted isocyanates may be prepared in known manner, for example, by reacting an amine with phosgene.

Examples of various compounds which may be used to form the $R^2$ radical of the compounds of the invention are the following:

methylamine, ethylamine, n-propylamine, 2-propylamine (isopropylamine), n-butylamine, sec-butylamine, isobutylamine, 2-methyl-2-propylamine (t-butylamine), n-amylamine, isoamylamine, n-hexylamine, n-heptylamine, n-octylamine, allylamine, n-butene-3-ylamine, 2-mercaptoethylamine, 3-mercapto-n-propylamine;

2-methoxyethylamine, 2-ethoxyethylamine, 2-propoxyethylamine, 2-butoxyethylamine, 2-pentoxyethylamine, 3-methoxypropylamine, 4-ethoxybutylamine, 5-propoxypentylamine, 6-ethoxyhexylamine, 7-methoxyheptylamine, 4-butyloxybutylamine, 2-methylthioethylamine, 2-ethylthioethylamine, (2-aminoethyl)methylsulfoxide, (2-aminoethyl)ethylsulfoxide, (3-aminopropyl)methylsulfoxide;

benzylamine, β-phenylethylamine, γ-phenyl-n-propylamine, phenylcyclopropylamine, 3-phenylcyclobutylamine, 2-phenylcyclopentylamine, 4-phenylcyclohexylamine, 1-phenylcycloheptylamine, 3-phenylcyclooctylamine;

cyclopentylamine, cyclohexylamine, cycloheptylamine, cyclooctylamine;

cyclopenten-2-ylamine, cyclohexen-3-ylamine, cyclohepten-4-ylamine, cycloocten-5-ylamine, 3-methylcyclohexylamine, 4-methylcyclohexen-3-ylamine;

2-aminodecalin, 1,2,4a,5,6,7,8,8a-octahydro-2-naphthylamine;

2-aminobicyclo[2,2,1]heptane, 2-aminobicyclo[2,2,1]-hept-5-ene, 3-aminobicyclo[3,1,1]heptane, 3-aminobicyclo[3,3,1]nonane, 3-aminobicyclo[3,3,1]-non-6-ene, 1-adamantylamine, 2-adamantylamine;

3-aminofuran, 3-aminotetrahydrofuran, 3-aminotetrahydropyran, 2-aminomethyltetrahydrofuran, 2-aminomethylfuran, 3-aminomethyltetrahydrofuran, 3-aminomethylfuran, 2-aminomethyltetrahydropyran, 3-aminomethyltetrahydropyran, 3-aminomethylpyran, 4-aminomethyltetrahydropyran;

3-aminothiophene, 3-aminotetrahydrothiophene, 3-aminotetrahydrothiopyran, 2-aminomethyltetrahydrothiophene, 2-aminomethyl-2,5-tetrahydrothiophene, 2-aminomethylthiophene, 3-aminomethyltetrahydrothiophene, 3-aminomethylthiophene, 2-aminomethyltetrahydrothiopyran, 3-aminomethyltetrahydrothiopyran, 3-aminomethylthiopyran, 4-aminomethyltetrahydrothiopyran.

The oxadiazolyl-sulfonylureas of the present invention are characterized by a strong and long-lasting blood-glucose lowering action in various mammalian species. In rats the oxadiazolylsulfonylureas of the present invention are from about 30 to about 100 times more potent than tolbutamide and have a potency comparable to that of glibenclamide. Consequently, compounds of Formula I may be used for the manufacture of orally administrable pharmaceutical preparations for the lowering of the blood sugar level in the treatment of diabetes mellitus and may be used as such or in the form of their physiologically tolerable salts or in the presence of substances which case such salt formation. For the formation of salts, there may be used, for example, alkaline agents such as, for example, alkali metal hydroxides or alkaline earth metal hydroxides, alkali metal carbonates or bicarbonates or also organic bases, in particular tertiary nitrogen bases, provided the resulting salts are physiologically tolerable.

The invention, therefore, also provides pharmaceutical preparations for treatment of diabetes mellitus which comprise a compound of the present invention in admixture or conjunction with a pharmaceutically suitable carrier.

The pharmaceutical preparations are advantageously in the form of tablets and the pharmaceutically suitable carrier may be, for example, talc, starch, lactose, tragacanth or magnesium stearate.

A pharmaceutical preparation containing a compound of the present invention as active substance, for example, a tablet or a powder, with or without the aforesaid carriers is advantageously brought into a suitable unit dosage form. The dose chosen should comply with the activity of the specific compound used and the desired effect. Advantageously, the dosage per unit amounts to from about 0.5 to about 500 mg per kg of body weight, preferably from about 2 to about 150 mg. but considerably higher or lower dosage units may also be used, which, if desired, are divided or multiplied prior to their administration.

The following examples illustrate the invention without, however, limiting the same thereto. All temperatures given are in degrees Centrigrade unless otherwise indicated.

EXAMPLE 1

1-Cyclohexyl-3-[p-β-(5-methyl-1,2,4-oxadiazole-3-carbonylaminoethyl)phenyl]sulfonyl]urea

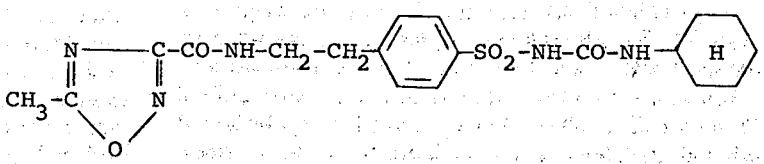

A. p-[β-(5-Methyl-1,2,4-oxadiazole-3-carbonylamino)ethyl]-benzenesulfonamide

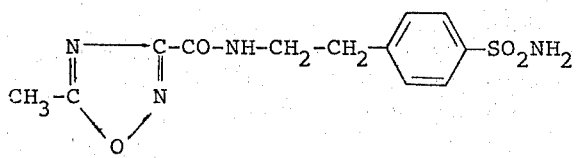

10 g p-(β-Aminoethyl)-benzenesulfonamide are combined with 7.1 g 5-methyl-1,2,4-oxadiazol-3-carboxylic acid methyl ester in 50 ml dimethylformamide and stirred overnight. On dilution with water and filtration, a precipitate is obtained. Yield: 14.6 g p-[β-(5-methyl-1,2,4-oxadiazole-3-carbonylamino)ethyl]-benzenesulfonamide (=94% of theory), M.P. 201°–203°C. On recrystallization from glycol monomethyl ether, the melting point is substantially unchanged.

B. 1-Cyclohexyl-3-[p-β-(5-methyl-1,2,4-oxadiazole-3-carbonylaminoethyl)phenylsulfonyl]urea 13.9 g p-[β-(5-Metyl-1,2,4-oxadiazole-3-carbonylamino)ethyl]-benzenesulfonamide are dissolved in a mixture of 45 ml of 1 N sodium hydroxide and 112 ml acetone at a temperature of from 5°–10°C. 5.9 g of cyclohexylisocyanate dissolved in 45 ml acetone are added dropwise and stirred overnight at room temperature. The acetone is distilled off on a rotary evaporator and the residue dissolved in 500 ml of water. The aqueous solution has a pH of 9.5 which is adjusted to 10.5 by adding some NaOH. The insoluble portions consisting of unreacted starting material admixed with dicyclohexylurea are then filtered off and the filtrate acidified with 2 N HCl. The precipitate which forms is filtered off and washed with water. Yield: 18 g of crude 1-cyclohexyl-3-[p-β-(5-methyl-1,2,4-oxadiazole-3-carbonylaminoethyl)phenylsulfonyl]urea. The purification of the crude product is effected by elutriation in 200 ml of methanol and solubilization through addition of 2 N sodium methylate solution. The solution is filtered and mixed with 2 N HCl while cooling with ice water. The crystallized pure product is filtered and washed with methanol and with water. Yield: 13 g (= 67% of theory), M.P. 189°–191°C.

EXAMPLE 2

1-Cyclohexyl-3-[p-β-(5-ethyl-1,2,4-oxadiazole-3-carbonylaminoethyl)phenylsulfonyl]urea

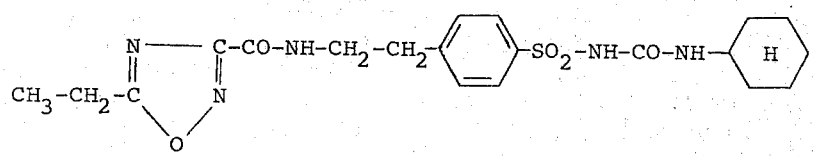

A. p-[β-(5-Ethyl-1,2,4-oxadiazole-3-carbonylamino)ethyl]-benzenesulfonamide

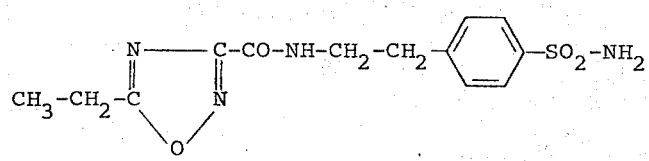

Following the procedure of Example 1A, 5-ethyl-1,2,4-oxadiazol-3-carboxylic acid methyl ester is reacted wth p-(β-aminoethyl)-benzenesulfonamide to yield p-[β-(5-ethyl-1,2,4-oxadiazole-3-carbonylamino)ethyl]-benzenesulfonamide in almost quantitative yield, M.P. 159°–160°C. The compound can be recrystallized from methanol.

B. Following the procedure of Example 1B, 16.2 g of the product from Example 2A are reacted with 6.55 g cyclohexylisocyanate to yield 15.7 g of analytically pure 1-cyclohexyl-3-[p-β-(5-ethyl-1,2,4-oxadiazole-3-carbonylaminoethyl)phenylsulfonyl]urea (= 70% of the theoretical yield), M.P. 196°C.

EXAMPLE 3

1-Cyclohexyl-3-[p-β-(3-phenyl-1,2,4-oxadizole-5-carbonylaminoethyl)phenylsulfonyl]urea

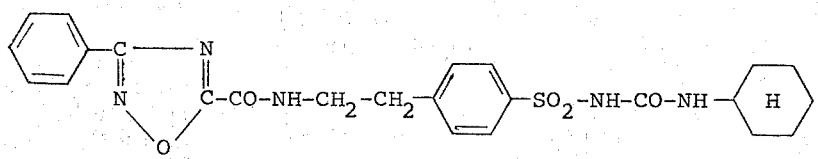

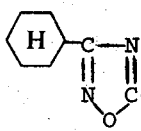 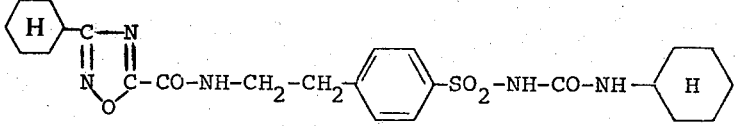

A. p-[B-(3-Phenyl-1,2,4-oxadiazole-5-carbonylamino)ethyl]benzenesulfonamide

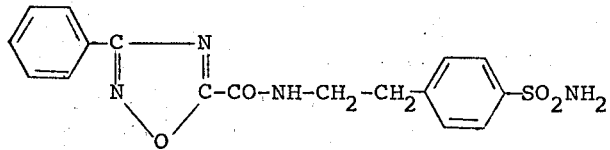

Following the procedure of Example 1A but employing as reactants 3-phenyl-1,2,4-oxadiazole-5-carboxylic acid ethyl ester and p-(β-aminoethyl)-benenesulfonamide, there is obtained p-[β-(3-phenyl-1,2,4-oxadiazole-5-carbonylamino)ethyl]-benzenesulfonamide, M.P. 217°–218°C. The compound can be recrystallized from dioxane. B. Following the procedure of Example 1B, the product from Example 3A is reacted with cyclohexylisocyanate to yield 1-cyclohexyl-3-[p-β-(3-phenyl-1,2,4-oxadiazol-5-carbonylaminoethyl)-phenylsulfonyl]urea, M.P. 195°–196°C.

EXAMPLE 4

1-Cyclohexyl-3-[p-β-(3-methyl-1,2,4-oxadiazole-5-carbonylaminoethyl)phenylsulfonyl]urea

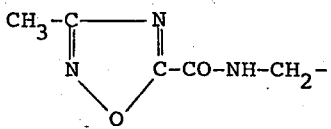

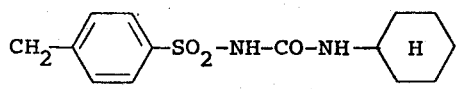

A. p-[β-(3-Methyl-1,2,4-oxadiazole-5-carbonylamino)ethyl]benzenesulfonamide

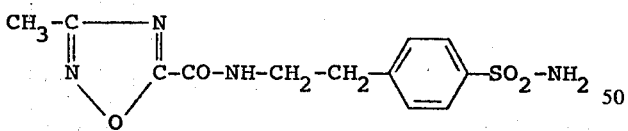

Following the procedure of Example 1A but employing as reactants 3-methyl-1,2,4-oxadiazole-5-carboxylic acid ethyl ester and p-(β-aminoethyl)-benzenesulfonamide, there is obtained p-(β-(3-methyl-1,2,4-oxadiazole-5-carbonylamino)ethyl]-benzenesulfonamide, M.P. 218°–220°C.

B. Following the procedure of Example 1B, the product from Example 4A is reacted with cyclohexylisocyanate to yeild 1-cyclohexyl-3-[p-β-(3-methyl-1,2,4-oxadiazole-5-carbonylaminoethyl)phenylsulfonyl]urea, M.P. 188°–190°C.

EXAMPLE 5

1-Cyclohexyl-3-[p-β-(3-cyclohexyl-1,2,4-oxadiazole-5-carbonylaminoethyl)phenylsulfonyl]urea A. p-[β-(3-Cyclohexyl-1,2,4-oxadiazole-5-carbonylamino)ethyl]benzenesulfonamide

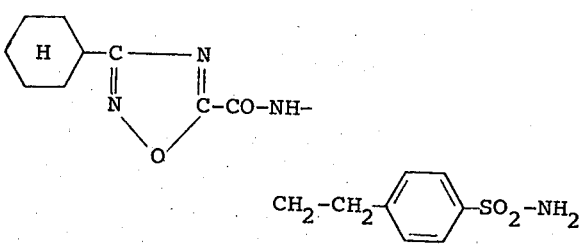

Following the procedure of Example 1A but employing as reactants 3-cyclohexyl-1,2,4-oxadiazole-5-carboxylic acid ethyl ester and p-(β-aminoethyl)-benzenesulfonamide, there is obtained p-[3-(cyclohexyl-1,2,4-oxadiazole-5-carbonylamino)ethyl]-benzenesulfonamide, M.P. 160°–162°C B. Following the procedure of Example 1B, the product from Example 5A is reacted with cyclohexylisocyanate to yield 1-cyclohexyl-3-[p-β-(3-cyclohexyl-1,2,4-oxadiazole-5-carbonylaminoethyl)phenylsulfonyl]urea, M.P. 170°–172°C.

EXAMPLE 6

1-Cyclohexyl-3-[p-β-(5-methyl-1,2,4-oxadiazole-3-carbonylaminomethyl)phenylsulfonyl]urea The title compound is obtained following the procedure of Example 1 but substituting an equivalent amount of p-(β-aminomethyl)-benzenesulfonamide for the p-(β-aminoethyl)-benzenesulfonamide in part A.

EXAMPLE 7

1-Cyclohexyl-3-[p-β-(3-phenyl-1,2,4-oxadiazole-5-carbonylamino-n-propyl)phenylsulfonyl]urea The title compound is obtained following the procedure of Example 3 but substituting an equivalent amount of p-β-(amino-n-propyl)-benzenesulfonamide for the p-(β-aminoethyl)benzenesulfonamide in part A.

EXAMPLE 8

1-(4-Methylcyclohexyl)-3-[p-β-(3-cyclohexyl-1,2,4-oxadiazole-5-carbonylaminoethyl)phenylsulfonyl]urea The title compound is obtained following the procedure of Example 5 but substituting 4-methylcyclohexylisocyanate for cyclohexylisocyanate.

EXAMPLES 9–21

Following the procedure of Example 1 but substituting for cyclohexylisocyanate the isocyanate of the formula $R^2NCO$ wherein $R^2$ is the radical listed in the following column, there is obtained the compound of the following formula wherein $R^2$ is the radical listed in the following column:

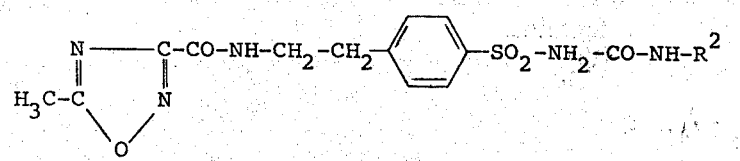

| Example | R² |
|---|---|
| 9 | cyclooctyl |
| 10 | cyclopentyl |
| 11 | cycloheptyl |
| 12 | cyclopropyl |
| 13 | cyclobutyl |
| 14 | trans-phenylcyclopropyl |
| 15 | β-phenethyl |
| 16 | propyl |
| 17 | ethyl |
| 18 | methyl |
| 19 | hexyl |
| 20 | pentyl |
| 21 | adamantyl |

EXAMPLES 22–43

Following the procedure of Example 1 but substituting for 5-methyl-1,2,4-oxadiazole-3-carboxylic acid methyl ester a 5-substituted 1,2,4-oxadiazole-3-carboxylic acid methyl ester wherein the 5-substituent is the radical indicated in the column below, the corresponding 1-cyclohexyl-3-[p-β-(5-substituted-1,2,4-oxadiazole-3-carbonylaminoethyl)phenylsulfonyl]urea is obtained.

| Example | Substituent |
|---|---|
| 22 | cyclopropyl-CH₂– |
| 23 | cyclopentyl-CH₂– |
| 24 | cyclopentyl-CH(CH₃)– |
| 25 | 2-methylphenyl |
| 26 | 4-methylphenyl |
| 27 | 3-isopropylphenyl |
| 28 | 2-fluorophenyl |
| 29 | 4-fluorophenyl |
| 30 | 4-chlorophenyl |
| 31 | 4-bromophenyl |
| 32 | 3-bromophenyl |
| 33 | 3-methoxyphenyl |
| 34 | 2,6-dimethylphenyl |
| 35 | 2,3-dimethoxyphenyl |
| 36 | 2-chloro-5-methoxyphenyl |
| 37 | 2-bromo-3-methylphenyl |
| 38 | 4-chloro-3-methoxy-6-methylphenyl |
| 39 | 4-chlorophenyl-CH₂– |
| 40 | 2-isopropylphenyl |

| Example | | Example | |
|---|---|---|---|
| 41 | 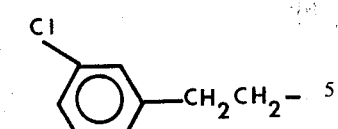 | 51 | 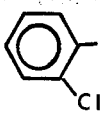 |
| 42 | 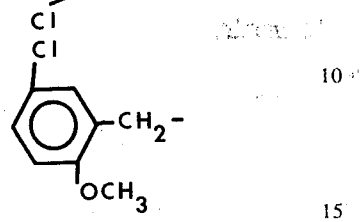 | 52 | 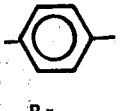 |
| | | 53 | 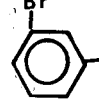 |
| 43 | 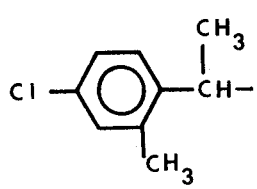 | 54 | 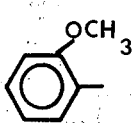 |
| | | 55 | 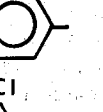 |
| | | 56 | 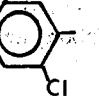 |
| | | 57 | 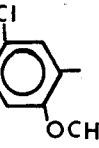 |

EXAMPLES 44–65

Following the procedure of Example 3 but substituting for 3-phenyl-1,2,4-oxadiazole-5-carboxylic acid ethyl ester a 3-substituted -1,2,4-oxadiazole-5-carboxylic acid methyl ester wherein the 3-substituent is the radical indicated in the column below, the corresponding 1-cyclohexyl-3-[-β-(3-substituted 1,2,4-oxadiazole-5-carbonylaminoethyl)phenylsulfonyl]urea is obtained.

| Example | | Example | |
|---|---|---|---|
| 44 |  | 58 | 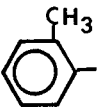 |
| 45 | 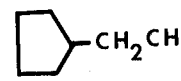 | 59 | 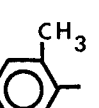 |
| 46 | 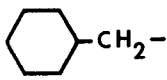 | 60 | 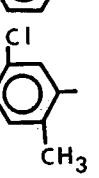 |
| 47 | 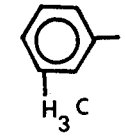 | 61 | 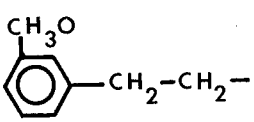 |
| 48 | 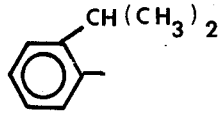 | 62 | 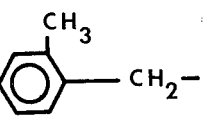 |
| 49 | 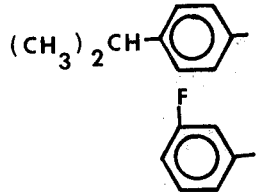 | 63 | 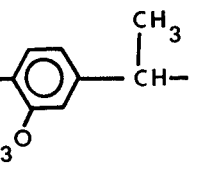 |
| 50 | | | |

| Example | |
|---|---|
| 64 | 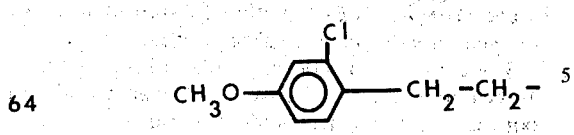 |
| 65 | 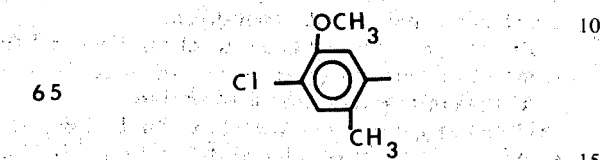 |

EXAMPLES 66–77

Following the procedure of Example 1 but substituting for cyclohexylisocyanate the isocyanate of the formula $R^2$ NCO wherein $R^2$ is the radical listed in the following column, there is obtained the compound of the following formula wherein $R^2$ is the radical listed in the following column:

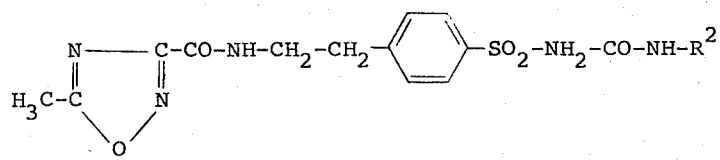

| Example | $R^2$ |
|---|---|
| 66 | allyl |
| 67 | 2-mercaptoethyl |
| 68 | 2-methoxyethyl |
| 69 | 2-methylthioethyl |
| 70 | benzyl |
| 71 | 3-phenylcyclopentyl |
| 72 | 4-phenylcyclohexyl |
| 73 | cyclopenten-2-yl |
| 74 | 2-decalin |
| 75 | 2-aminobicyclo[2,2,1]heptyl |
| 76 | 3-furyl |
| 77 | 3-thienyl. |

EXAMPLE 78

A tablet for pharmaceutical administration is prepared from the following ingredients:

| Ingredient | Parts by wt. |
|---|---|
| 1-Cyclohexyl-3-[p-β-(5-methyl-1,2,4-oxadiazole-3-carbonylaminoethyl)phenylsulfonyl]urea | 0.100 |
| Magnesium stearate | 0.0010 |
| Polyvinyl pyrrolidone | 0.0040 |
| Talcum | 0.0050 |
| Maize starch | 0.010 |
| Lactose | 0.038 |
| Dimethyl silicone oil | 0.0005 |
| Polyethylene glycol-6000 | 0.0015 |

What is claimed is:
1. A compound of the formula

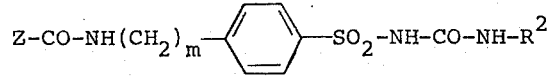

wherein
Z is an oxadiazole radical of the formula

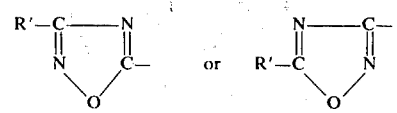

wherein R' is hydrogen, a straight or branched chain alkyl or alkenyl radical of from 1 to 6 carbon atoms, a cycloalkyl radical of from 3 to 6 carbon atoms, cycloalkyl-alkyl wherein the cycloalkyl moiety has from 3 to 6 carbon atoms and the alkyl moiety has from 1 to 4 carbon atoms, $(R^3)_n$-phenyl, $(R^3)_n$-pheylalkyl wherein the akyl moiety has from 1 to 4 carbon atoms, $R^3$ is hydrogen, an alkyl or alkoxy radical of from 1 to 4 carbon atoms, or halogen, and $n$ is 0, 1 or 2;
$m$ is 1, 2 or 3; and
$R^2$ is
1. hydrogen, a straight or branched chain alkyl or alkenyl radical of from 1 to 6 carbon atoms, mercaptoalkyl of from 2 to 8 carbon atoms, or phenyl;
2. a radical of the formula

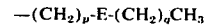

wherein E is oxygen, sulfur or sulfonyl, $p$ is from 2 to 7, and $q$ is 0 to 5, the sum of $p + q$ being from 3 to 7;
3. phenylalkyl wherein the alkyl radical has from 1 to 3 carbon atoms or phenylcycloalkyl wherein the cycloalkyl radical has from 3 to 8 carbon atoms;
4. cycloalkyl or cycloalkenyl of from 3 to 8 carbon atoms or alkyl-substituted cycloalkyl or cycloalkenyl wherein the alkyl radical has from 1 to 3 carbon atoms;
5. endoalkylene cycloalkyl, endoalkylene cycloalkenyl, bisendoalkylene cycloalkyl or bisendoalkylene cycloalkenyl wherein the endoalkylene part has from 1 to 4 carbon atoms and the cycloalkyl or cycloalkenyl part has from 5 to 8 carbon atoms;
6. a saturated, mono- or di-unsaturated heterocyclic ring containing from 4 to 6 carbon atoms and an oxygen atom or a sulfur atom or a nitrogen atom
7. a saturated, mono- or di-unsaturated heterocyclic ring linked to the nitrogen atom by means of a methylene group and containing from 4 to 5 carbon atoms and either an oxygen or a sulfur atom.
2. A compound of claim 1 wherein Z is

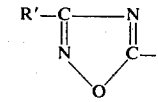

wherein R' is as defined in claim 1.

3. A compound of claim 1 wherein Z is

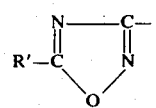

wherein R' is as defined in claim 1.

4. A compound according to claim 1 wherein $m$ is 2.

5. A compound according to claim 1 wherein $R^2$ is alkyl of from 1 to 6 carbon atoms or cycloalkyl of from 3 to 8 carbon atoms.

6. A compound according to claim 1 wherein $m$ is 2 and $R^2$ is alkyl of from 1 to 6 carbon atoms or cycloalkyl of from 3 to 8 carbon atoms.

7. A compound according to claim 1 having the name 1-cyclohexyl-3-[p-β-(5-methyl-1,2,4-oxadiazole-3-carbonylaminoethyl)phenylsulfonyl]urea.

8. A compound according to claim 1 having the name 1-cyclohexyl-3-[p-β-(5-ethyl-1,2,4-oxadiazole-3-carbonylaminoethyl)phenylsulfonyl]urea.

9. A compound according to claim 1 having the name 1-cyclohexyl-3-[p-β-(3-phenyl-1,2,4-oxadiazole-5-carbonylaminoethyl)phenylsulfonyl]urea.

10. A compound according to claim 1 having the name 1-cyclohexyl-3-[p-β-(3-methyl-1,2,4-oxadiazole-5-carbonylaminoethyl)phenylsulfonyl]urea.

11. A compound according to claim 1 having the name 1-cyclohexyl-3-[p-β-(3-cyclohexyl-1,2,4-oxadiazole-5-carbonylaminoethyl)phenylsulfonyl]urea.

* * * * *